US012606584B2

(12) United States Patent
Fettes et al.

(10) Patent No.: US 12,606,584 B2

(45) Date of Patent: Apr. 21, 2026

(54) PROCESS FOR THE PREPARATION OF OLIGONUCLEOTIDES USING MODIFIED OXIDATION PROTOCOL

(71) Applicant: Hoffmann-La Roche Inc., Little Falls, NJ (US)

(72) Inventors: Alec Fettes, Maur (CH); Achim Geiser, Seon (CH); Leonhard Jaitz, Oeschgen (CH); Hongrim Choi, Seoul (KR); Kyeong Eun Jung, Seoul (KR); Sung Won Kim, Seoul (KR)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 1104 days.

(21) Appl. No.: 17/617,819

(22) PCT Filed: Jun. 9, 2020

(86) PCT No.: PCT/EP2020/065992

§ 371 (c)(1),
(2) Date: Dec. 9, 2021

(87) PCT Pub. No.: WO2020/249571

PCT Pub. Date: Dec. 17, 2020

(65) Prior Publication Data

US 2023/0295207 A1 Sep. 21, 2023

(30) Foreign Application Priority Data

Jun. 11, 2019 (EP) .................................... 19179310

(51) Int. Cl.
*C07H 1/00* (2006.01)
*C07H 21/02* (2006.01)
*C07H 21/04* (2006.01)

(52) U.S. Cl.
CPC ............... *C07H 1/00* (2013.01); *C07H 21/02* (2013.01); *C07H 21/04* (2013.01)

(58) Field of Classification Search
None
See application file for complete search history.

(56) References Cited

U.S. PATENT DOCUMENTS

| | | | |
|---|---|---|---|
| 5,631,362 A | 5/1997 | Pfleiderer et al. | |
| 7,205,399 B1 | 4/2007 | Vargeese et al. | |
| 2004/0024194 A1 | 2/2004 | Ravikumar | |
| 2022/0251128 A1 * | 8/2022 | McPherson ............ | C07H 21/02 |

FOREIGN PATENT DOCUMENTS

| | | | |
|---|---|---|---|
| CN | 103298823 | A | 9/2013 |
| CN | 107474091 | A | 12/2017 |
| CN | 109641932 | A | 4/2019 |
| JP | H0-5320122 | | 12/1993 |
| JP | 2002-536453 | A | 10/2002 |
| JP | 2004-533488 | A | 11/2004 |
| KR | 10-1999-0022711 | | 3/1999 |
| WO | 96/040708 | A2 | 12/1996 |
| WO | 97/019092 | A1 | 5/1997 |
| WO | 99/018238 | | 4/1999 |
| WO | 00/047593 | A1 | 8/2000 |
| WO | 03/004512 | A1 | 1/2003 |
| WO | 2007/097446 | A1 | 8/2007 |
| WO | 2012/001126 | A1 | 1/2012 |
| WO | 2013/134686 | A1 | 9/2013 |
| WO | 2018/019799 | A2 | 2/2018 |
| WO | 2018/197533 | A1 | 11/2018 |
| WO | 2020/236618 | A1 | 11/2020 |

OTHER PUBLICATIONS

Beaucage, S., et al., "The synthesis of modified oligonucleotides by the phosphoramidite approach and their applications" Tetrahedron 49(28):6123-6194 (Jul. 9, 1993).
Grevys, A., et al., "A human endothelial cell-based recycling assay for screening of FcRn targeted molecules" Nat Commun 9(1):621 (1-14) (Feb. 12, 2018).
"International Preliminary Report on Patentability—PCT/EP2020/065992" (Report Issuance Date: Dec. 14, 2021; Chapter I), :pp. 1-8 (Dec. 23, 2021).
"International Search Report—PCT/EP2020/065992" (w/Written Opinion),: pp. 1-17 (Jul. 3, 2020).
Nath, N., et al., "Homogeneous plate based antibody internalization assay using pH sensor fluorescent dye" J Immunol Methods 431:11-21 (Apr. 1, 2016).
"Safety Data Sheet, Product Name: Oxidizing Reagent 0.05 M Iodine in Pyridine / Water 90/10b (vv) for DNA Synthesis Novabiochem®, Catalog No. BI0424," Sigma-Aldrich Japan, pp. 15 (Read on Apr. 19, 2023).
Oxidizing Reagent, 0.05M, $I_2$ in Pyridine Biosynthesis Novabiochem®, Catalog No. BI0424, Sigma-Aldrich, Japan, Internet, https://www.sigmaaldrich.com/JP/ja/product/mm/bi0424, pp. 6 (Read on Apr. 19, 2023).
Sato et al., Wakou Jun'yaku jihou 86(4):12-13 (Oct. 2018).
Wei et al., "Coupling activators for the oligonucleotide synthesis via phosphoramidite approach" Tetrahedron 69:3615-3637 ( 2013).

* cited by examiner

*Primary Examiner* — Bahar Craigo
(74) *Attorney, Agent, or Firm* — Daniel Shelton

(57) ABSTRACT

The invention relates to a process for the production of a mixed P═O/P═S backbone oligonucleotide comprising a selective oxidation of an intermediary phosphite triester compound of formula I into a phosphodiester compound of formula II according to the scheme with an oxidation solution obtained by mixing iodine, an organic solvent and water, characterized in that the oxidation solution has been aged for a time period that is sufficient to selectively oxidize the phosphite triester compound of formula I into the phosphodiester compound of formula II without oxidizing the phosphorothioate internucleotide linkages.

10 Claims, No Drawings

Specification includes a Sequence Listing.

PROCESS FOR THE PREPARATION OF OLIGONUCLEOTIDES USING MODIFIED OXIDATION PROTOCOL

CROSS-REFERENCE TO RELATED APPLICATIONS

This application is a National Stage Entry under 35 U.S.C. § 371 of International Application No. PCT/EP2020/065992, filed Jun. 9, 2020, which claims benefit to European Application No. 19179310.8, filed on Jun. 11, 2019, each of which is incorporated herein by reference in its entirety and for all purposes.

SEQUENCE LISTING

This application contains a Sequence Listing which has been submitted electronically in ASCII format and is hereby incorporated by reference in its entirety. Said ASCII copy, created on Aug. 26, 2022, is named P35593US_Seq_List_Amended.txt and is 563 bytes in size.

SUMMARY

The invention relates to a novel process for the production of a mixed P═O/P═S backbone oligonucleotide comprising the oxidation of an intermediary phosphite triester compound of formula I into a phosphodiester compound of formula II according to the scheme

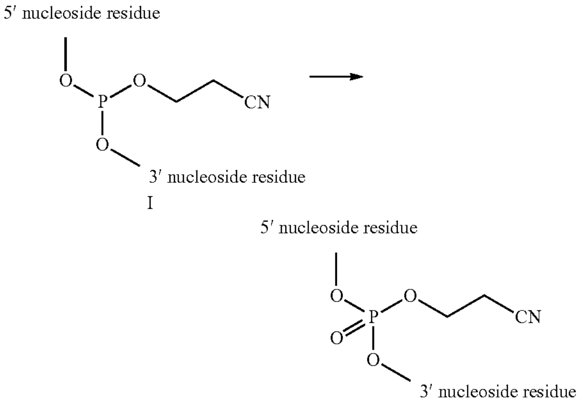

I

II wherein the oxidation follows a particular oxidation protocol.

The oligonucleotide synthesis in principle is a stepwise addition of nucleotide residues to the 5'-terminus of the growing chain until the desired sequence is assembled.

As a rule, each addition is referred to as a synthetic cycle and in principle consists of the chemical reactions $a_1$) $_{de}$-blocking the protected hydroxyl group on the solid support, $a_2$) coupling the first nucleoside as activated phosphoramidite with the free hydroxyl group on the solid support, $a_3$) oxidizing or sulfurizing the respective P-linked nucleoside (phosphite triester) to form the respective phosphodiester (P═O) or the respective phosphorothioate (P═S);

$a_4$) optionally, capping any unreacted hydroxyl groups on the solid support;

$a_5$) de-blocking the 5' hydroxyl group of the first nucleoside attached to the solid support;

$a_6$) coupling the second nucleoside as activated phosphoramidite to form the respective P-linked dimer;

$a_7$) oxidizing or sulfurizing the respective P-linked dinucleotide (phosphite triester) to form the respective phosphodiester (P═O) or the respective phosphorothioate (P═S);

$a_8$) optionally, capping any unreacted 5' hydroxyl groups;

$a_9$) repeating the previous steps as to as until the desired sequence is assembled.

The principles of the oligonucleotide synthesis are well known in the art (see e.g. Oligonucleotide synthesis; Wikipedia, the free encyclopedia; https://en.wikipedia.org/wiki/Oligonucleotide synthesis, of Mar. 15, 2016).

The oxidizing step is typically performed with an oxidation solution comprising iodine, an organic solvent, which as a rule is pyridine and water.

However, it was observed that when a freshly prepared oxidation solution has been applied, not only the desired oxidation of the intermediary phosphite triester compound of formula I into a phosphodiester compound of formula II takes place, but also, as a side reaction, phosphorothioate internucleotide linkages present in the molecule may be affected by a P═S to P═O conversion at the internucleotide linkages which resulted in a higher than expected content of phosphodiester linkages within the compound of formula II.

Object of the invention therefore was to find an oxidation protocol which allows a selective oxidation of the phosphite triester compound of formula I into the phosphodiester compound of formula II without affecting the phosphorothioate internucleotide linkage.

It was found that the object of the invention could be reached with the process for the production of a mixed P═O/P═S backbone oligonucleotide which comprises the oxidation of an intermediary phosphite triester compound of formula I into a phosphodiester compound of formula II according to the scheme

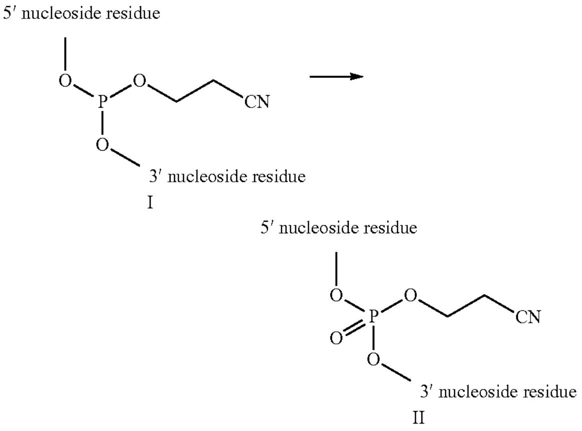

I

II with an oxidation solution obtained by mixing iodine, an organic solvent, and water, and which is characterized in that the oxidation solution has been aged for a time period that is sufficient to selectively oxidize the phosphite triester compound of formula I into the phosphodiester compound of formula II without oxidizing the phosphorothioate internucleotide linkages.

The following definitions are set forth to illustrate and define the meaning and scope of the various terms used to describe the invention herein.

The term "$C_{1-6}$-alkyl" denotes a monovalent linear or branched saturated hydrocarbon group of 1 to 6 carbon atoms, and in a more particular embodiment 1 to 4 carbon atoms. Typical examples include methyl, ethyl, propyl, isopropyl, n-butyl, i-butyl, sec-butyl, or t-butyl, preferably methyl or ethyl.

The term oligonucleotide as used herein is defined as it is generally understood by the skilled person as a molecule comprising two or more covalently linked nucleotides. For use as a therapeutically valuable oligonucleotide, oligonucleotides are typically synthesized as 10 to 40 nucleotides, preferably 10 to 25 nucleotides in length.

The oligonucleotides may consist of optionally modified DNA or RNA nucleoside monomers or combinations thereof.

Optionally modified as used herein refers to nucleosides modified as compared to the equivalent DNA or RNA nucleoside by the introduction of one or more modifications of the sugar moiety or the nucleobase moiety.

Typical modifications can be the 2'-O-(2-Methoxyethyl)-substitution (2'-MOE) substitution in the sugar moiety or the locked nucleic acid (LNA), which is a modified RNA nucleotide in which the ribose moiety is modified with an extra bridge connecting the 2' oxygen and the 4' carbon.

The term modified nucleoside may also be used herein interchangeably with the term "nucleoside analogue" or modified "units" or modified "monomers".

The DNA or RNA nucleotides are as a rule linked by a phosphodiester (P═O) or a phosphorothioate (P═S) internucleotide linkage which covalently couples two nucleotides together.

In accordance with the invention at least one internucleotide linkage has to consist of a phosphorothioate (P═S). Accordingly, in some oligonucleotides all other internucleotide linkages may consist of a phosphodiester (P═O) or in other oligonucleotides the sequence of internucleotide linkages vary and comprise both phosphodiester (P═O) and phosphorothioate (P═S) internucleotide linkages.

Accordingly the term mixed P═O/P═S backbone oligonucleotide refers to oligonucleotides wherein at least one internucleotide linkage has to consist of a phosphorothioate (P═S).

The nucleobase moieties may be indicated by the letter code for each corresponding nucleobase, e.g. A, T, G, C or U, wherein each letter may optionally include modified nucleobases of equivalent function. For example, in the exemplified oligonucleotides, the nucleobase moieties are described with capital letters A, T, G and MeC (5-methyl cytosine) for LNA nucleoside and with small letters a, t, g, c and MeC for DNA nucleosides. Modified nucleobases include but are not limited to nucleobases carrying protecting groups such as tert-butylphenoxyacetyl, phenoxyacetyl, benzoyl, acetyl, isobutyryl or dimethylformamidino (see Wikipedia, Phosphoramidit-Synthese, https://de.wikipedia.org/wiki/Phosphoramidit-Synthese of Mar. 24, 2016).

Preferably the oligonucleotide consists of optionally modified DNA or RNA nucleoside monomers or combinations thereof and is 10 to 40, preferably 10 to 25 nucleotides in length.

The principles of the oligonucleotide synthesis are well known in the art (see e.g. Oligonucleotide synthesis; Wikipedia, the free encyclopedia; https://en.wikipedia.org/wiki/Oligonucleotide synthesis, of Mar. 15, 2016).

Larger scale oligonucleotide synthesis nowadays is carried out in an automated manner using computer-controlled synthesizers.

As a rule, oligonucleotide synthesis is a solid-phase synthesis, wherein the oligonucleotide being assembled is covalently bound, via its 3'-terminal hydroxy group, to a solid support material and remains attached to it over the entire course of the chain assembly. Suitable supports are the commercial available macroporous polystyrene supports like the Primer support 5G from GE Healthcare or the NittoPhase® HL support from Kinovate.

The subsequent cleavage from the resin can be performed with concentrated aqueous ammonia. The protecting groups on the phosphate and the nucleotide base are also removed within this cleavage procedure.

As outlined above the process for the production of a mixed P═O/P═S backbone oligonucleotide is comprising the oxidation of an intermediary phosphite triester compound of formula I into a phosphodiester compound of formula II according to the scheme

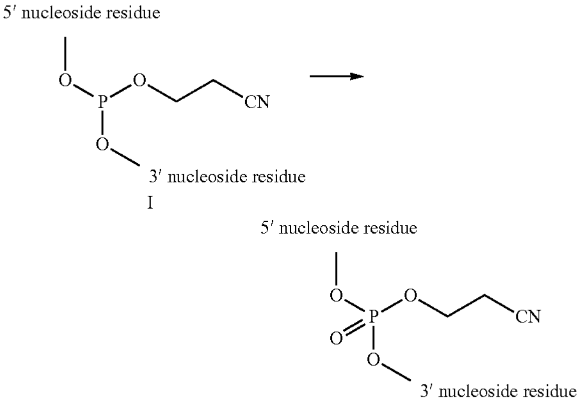

I

II with an oxidation solution obtained by mixing iodine, an organic solvent, and water and is characterized in that the oxidation solution has been aged for a time period that is sufficient to selectively oxidize the phosphite triester compound of formula I into the phosphodiester compound of formula II without oxidizing the phosphorothioate internucleotide linkages.

The mixed P═O/P═S backbone oligonucleotide comprises at least one phosphorothioate internucleotide linkage.

The oxidation solution is typically a solution which can be obtained by mixing iodine, an organic solvent, and water.

The organic solvent can be selected from pyridine or from a $C_{1-6}$ alkyl-substituted pyridine e.g. lutidine, but preferably from pyridine. A further organic solvent such as tetrahydrofuran may be present.

The oxidation solutions are commercially available, e.g. as oxidizer solutions from Sigma Aldrich (Merck). Alternatively, fresh solutions can be prepared using commercially available iodine and pyridine.

The volume ratio of pyridine or $C_{1-6}$ alkyl-substituted pyridine to water can vary in a range from 1:1 to 20:1, preferably from to 5:1 to 15:, but more preferably is 9:1.

The iodine concentration in the oxidation solution can be in the range of 10 mM to 100 mM, more preferably in the range between 20 mM to 50 mM.

The optimal period for the aging is largely determined by the temperature at which the oxidation solution is aged. While a low aging temperature results in longer aging period, a higher aging temperature significantly reduces the aging time.

It was found that the aging of the oxidation solution can take place at a temperature of 20° C. to 100° C., but preferably at a temperature of 30° C. to 60° C.

The time period required for the aging of the oxidation solution has to be sufficient to effect selective oxidation of the phosphite triester compound of formula I into the phosphodiester compound of formula II without oxidizing the phosphorothioate internucleotide linkages.

As a rule the oxidation solution can be aged for a time period of at least 1 day, 3 days, 5 days, 10 days, 15 days or at least 20 days.

The time period may, as mentioned, largely varies dependent on the aging temperature and can for an aging temperature of 30° C. to 35° C. vary between 10 days and 150 days, more typically between 20 days and 60 days, while for an aging temperature of 60° C. to 65° C. can vary between 1 day and 30 days, more typically between 2 and 15 days.

The aging as a rule goes along with an increase of the conductivity (μS/cm) and a decrease of the pH. In a further embodiment of the invention the process of the present invention comprises the monitoring of the parameters pH and conductivity to determine the time period that is sufficient to selectively oxidize the phosphite triester compound of formula I into the phosphodiester compound of formula II without oxidizing the phosphorothioate internucleotide linkages.

The amount of oxidant used in the oxidation reaction can be selected between 1.1 equivalents and 15 equivalents, more preferably between 1.5 equivalents and 4.5 equivalents, most preferably between 2 equivalents and 4 equivalents.

As a rule the oxidation reaction temperature is performed between 15° C. and 27° C., more preferably between 18° C. and 24° C.

By way of illustration the oligonucleotide can be selected from:

$5'\text{-}{}^{Me}\underline{C}_S\ {}^{Me}\underline{U}_O\ {}^{Me}\underline{C}_O\underline{A}_O\underline{G}_S T_S A_S A_S\ {}^{Me}C_S A_S T_S T_S G_S A_S\ {}^{Me}C_S\underline{A}_O\ {}^{Me}\underline{C}_O\ {}^{Me}\underline{C}_O\underline{A}_S\ {}^{Me}\underline{C}\text{-}3'$ The underlined residues are 2'-MOE nucleosides. The locations of phosphorothioate and phosphate diester linkages are designated by S and O, respectively. It should be noted that 2'-O-(2-methoxyethyl)-5-methyluridine (2'-MOE MeU) nucleosides are sometimes referred to as 2'-O-(2-methoxyethyl) ribothymidine (2'-MOE T).

The compounds disclosed herein have the following nucleobase sequences

SEQ ID No. 1: cucagtaacattgacaccac

EXAMPLES

Example 1

Synthesis of $5'\text{-}{}^{Me}\underline{C}_S\ {}^{Me}\underline{U}_O\ {}^{Me}\underline{C}_O\underline{A}_O\underline{G}_S T_S A_S A_S\ {}^{Me}C_S A_S\text{-}T_S T_S G_S A_S\ {}^{Me}C_S\underline{A}_O\ {}^{Me}\underline{C}_O\ {}^{Me}\underline{C}_O\underline{A}_S\ {}^{Me}\underline{C}\text{-}3'$ The oligonucleotide was produced by standard phosphoramidite chemistry on solid phase at a scale of 2.20 mmol using an AKTA Oligopilot 100 and Primer Support Unylinker (NittoPhase LH Unylinker 330). In general 1.4 equiv of the DNA/2'-MOE-phosphoramidites were employed. Other reagents (dichloroacetic acid, 1-methylimidazole, 4,5-dicyanoimidazole, acetic anhydride, phenylacetyl disulfide, pyridine, triethylamine) were used as received from commercially available sources and reagent solutions at the appropriate concentration were prepared (see table 1 below) Cleavage and deprotection was achieved using ammonium hydroxide to give the crude oligonucleotide.

TABLE 1

| Standard Reagent Solutions | |
|---|---|
| Deblock | 10% dichloroacetic acid in toluene (v/v) |
| Phosphoramidites | 0.2M in acetonitrile |
| NMI/DCI activator | 1.0M 4,5-dicyanoimidazole/0.1M 1-methylimidazole in acetonitrile |
| Oxidizer | 0.05M iodine in pyridine/water 9:1 (v/v); purchased from Sigma Aldrich or freshly prepared (see examples) |
| Thiolation | 0.2M phenylacetyl disulfide in 3-picoline/acetonitrile (1:1 v/v) |
| Cap A | 1-Methylimidazole/pyridine/acetonitrile 2:3:5 (v/v/v) |
| Cap B | Acetic anhydride/acetonitrile 1:4 (v/v) |
| Amine wash | 50% triethylamine in acetonitrile (v/v) |
| Cleavage and Deprotection | 28-32% aqueous ammonium hydroxide |

Example 2

Oxidizer Aging Experiments

Example 2.1

With Purchased Oxidizer Solution

TABLE 2

| Oxidizer Batch 1 | | | Oxidizer Batch 2 | | |
|---|---|---|---|---|---|
| Example | Aging time at 30-35° C. (d) | Total (P = O)$_1$[3] content (%) | Example | Aging time at 30-35° C. (d) | Total (P = O)$_1$[3] content (%) |
| 2.1 | 0[1] | 7.8 | 3.1 | 0[1] | 14.8 |
| 2.2 | 3 | 3.5 | 3.2 | 3 | 9.3 |
| 2.3 | 6 | 1.8 | 3.3 | 6 | 4.5 |
| 2.4 | 9 | 1.7 | 3.4 | 9 | 3.4 |
| 2.5 | 16[2] | 4.5 | 3.5 | 16[2] | 11.6 |

[1] refers to the point in time when an aliquot from the commercial solution was taken for use-test and the thermal treatment of the remainder of the solution was started. This is not the same as the preparation time of the solution.

[2] the solution was not aged at 30-35° C. but stored at 1-15° C. starting at t = 0.

[3] refers to the percentage of molecules having a mass difference of 16 Da relative to the molecular mass of the desired compound determined in mass spectrometry, i.e. percentage of those molecule wherein 1 P = S linkage has been transformed into a P = O linkage.

Example 2.2

With Freshly Prepared Oxidizer Solution:

a) Preparation of Iodine Solution 1.00 kg of water were added to 8.00 kg of pyridine at room temperature. 127 g of iodine were added. 0.827 kg of pyridine were added for rinsing and the mixture was stirred for 1 h under a positive pressure of dry nitrogen.

b) Aging of Iodine Solution

Aging at 30-35° C.:

800 mL aliquots were stored at 30-35° C. in amber glass bottles until use.

Aging at 60-65° C.:

The material was kept in a jacketed glass reactor at 60-65° C. under a positive pressure of dry nitrogen until use.

TABLE 3

| (aging at 30° C.-35° C.) Oxidizer Batch aged at 30° C. to 35° C. | | | | |
|---|---|---|---|---|
| Example | Aging time at 30-35° C. (d) | Total (P = O)$_1$[2] content (%) | pH | Conductivity (□S/cm) |
| 2.6 | 0[1] | 15.0 | 7.31 | 186 |
| 2.7 | 9 | 8.2 | 6.38 | 1144 |
| 2.8 | 17 | 4.3 | 6.33 | 1440 |
| 2.9 | 29 | 2.0 | 6.21 | 1576 |
| 3.0 | 59 | 1.5 | 6.35 | 1654 |
| 3.1 | 122 | 1.2 | 6.18 | 1633 |

TABLE 4

| (aging at 60° C.-65° C.) Oxidizer Batch aged at 60° C. to 65° C. | | | | |
|---|---|---|---|---|
| Example | Aging time at 60-65° C. (d) | Total (P = O)$_1$[2] content (%) | pH | Conductivity (□S/cm) |
| 3.2 | 0[1] | 15.0 | 7.31 | 186 |
| 3.3 | 1 | 8.3 | 6.34 | 1215 |
| 3.4 | 3 | 1.5 | 6.21 | 1718 |
| 3.5 | 10 | 1.3 | 6.18 | 1970 |
| 3.6 | 30 | 1.2 | 6.09 | 2144 |

[1]refers to the point in time when the solution was preparation of the solution was completed.
[2]refers to the percentage of molecules having a mass difference of 16 Da relative to the molecular mass of the desired compound determined in mass spectrometry, i.e. percentage of those molecule wherein 1 P = S linkage has been transformed into a P = O linkage.

The invention claimed is:

1. A process of selectively oxidizing an intermediary phosphite triester in a mixed phosphodiester/phosphorothioate backbone oligonucleotide comprising:

preparing an oxidation solution comprising iodine, pyridine and water;

aging the oxidation solution for 1 day to 30 days at a temperature of 60° C. to 65° C. to produce an aged oxidation solution; and oxidizing an intermediary phosphite triester compound of formula I with the aged oxidation solution, thereby forming a phosphodiester compound of formula II according to the scheme

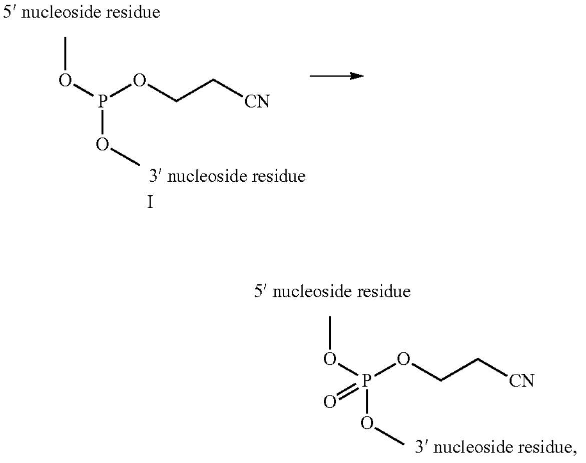

I

II wherein the 3' and/or 5' nucleoside residue comprises at least one phosphorothioate internucleotide linkage.

2. The method of claim 1, wherein the oxidation solution is aged for 2 days to 15 days at a temperature of 60° C. to 65° C. to produce an aged oxidation solution.

3. The method of claim 1, wherein the volume ratio of pyridine to water is from 1:1 to 20:1.

4. The method of claim 1, wherein the iodine concentration in the oxidation solution is 10 mM to 100 mM.

5. The method of claim 1, wherein the reaction temperature for the oxidizing step is selected between 15° C. and 27° C.

6. The method of claim 1, wherein the oligonucleotide consists of optionally modified DNA or RNA nucleoside monomers or combinations thereof and is 10 to 40 nucleotides in length.

7. The method of claim 3, wherein the volume ratio of pyridine to water is from 5:1 to 15:1.

8. The method of claim 3, wherein the volume ratio of pyridine to water is 9:1.

9. The method of claim 4, wherein the iodine concentration in the oxidation solution is 20 mM to 50 mM.

10. The method of claim 6, wherein the oligonucleotide consists of optionally modified DNA or RNA nucleoside monomers or combinations thereof and is 10 to 25 nucleotides in length.

* * * * *

SEQUENCE LISTING

<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide

<400> SEQUENCE: 1
cucagtaaca ttgacaccac 20